United States Patent [19]
Oroskar

[11] Patent Number: 5,811,622
[45] Date of Patent: *Sep. 22, 1998

[54] PROCESS FOR THE PRODUCTION OF DEHYDROGENATED HYDROCARBONS

[75] Inventor: Anil R. Oroskar, Downers Grove, Ill.

[73] Assignee: UOP, Des Plaines, Ill.

[ * ] Notice: The term of this patent shall not extend beyond the expiration date of Pat. No. 5,476,980.

[21] Appl. No.: 723,206

[22] Filed: Sep. 27, 1996

[51] Int. Cl.$^6$ ...................................................... C07C 5/42
[52] U.S. Cl. .......................... 585/656; 585/617; 585/654; 585/627
[58] Field of Search .................................. 585/654, 655, 585/656, 617, 627

[56] References Cited

U.S. PATENT DOCUMENTS

| | | | |
|---|---|---|---|
| 3,720,604 | 3/1973 | Rosback | 208/310 |
| 4,675,465 | 6/1987 | Fanelli et al. | 585/654 |
| 5,476,980 | 12/1995 | Oroskar | 585/654 |

*Primary Examiner*—Bekir L. Yildirim
*Attorney, Agent, or Firm*—Thomas K. McBride; John G. Tolomei; John G. Cutts, Jr.

[57] ABSTRACT

A process for the dehydrogenation of a dehydrogenatable hydrocarbon by (1) contacting the dehydrogenatable hydrocarbon with a liquid alkali metal in a dehydrogenation zone to produce a stream containing a dehydrogenated hydrocarbon and an unconverted dehydrogenatable hydrocarbon, and an alkali metal hydride; (2) heating the alkali metal hydride to produce a heated liquid alkali metal and hydrogen; (3) recycling the heated liquid alkali metal to the dehydrogenation zone; (4) contacting the stream containing dehydrogenated hydrocarbon and unconverted dehydrogenatable hydrocarbon with a selective adsorbent to produce a stream containing dehydrogenated hydrocarbon and a stream containing an unconverted hydrogenatable hydrocarbon; (5) recycling the stream of the unconverted dehydrogenatable hydrocarbon to the dehydrogenation zone; and (6) recovering the stream containing dehydrogenated hydrocarbon.

11 Claims, 1 Drawing Sheet

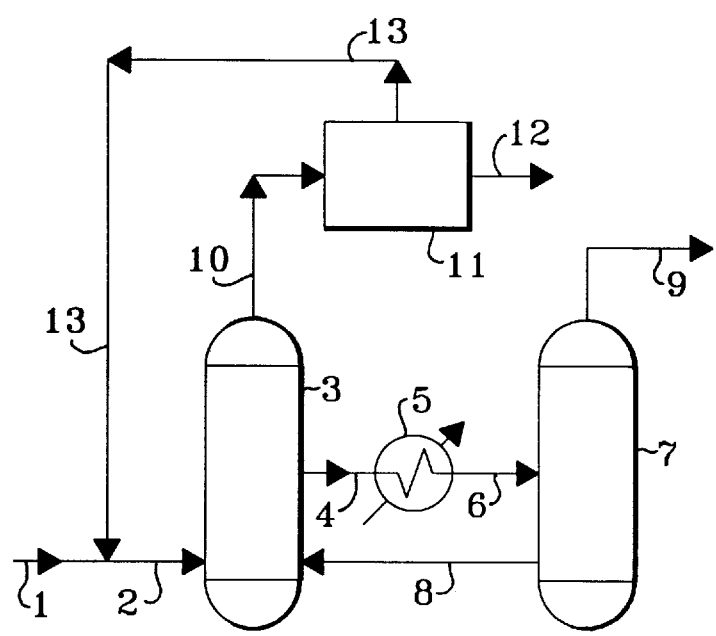

PROCESS FOR THE PRODUCTION OF DEHYDROGENATED HYDROCARBONS

FIELD OF THE INVENTION

The field of art to which this invention pertains is the production of dehydrogenated hydrocarbons by the dehydrogenation of dehydrogenatable hydrocarbons in a dehydrogenation zone. This invention relates more specifically to a process for the dehydrogenation of a dehydrogenatable hydrocarbon by contacting the dehydrogenatable hydrocarbon with a liquid comprising an alkali metal in a dehydrogenation zone to produce a hydrocarbon stream containing dehydrogenated hydrocarbons and an alkali metal hydride. The resulting alkali metal hydride is heated to produce a heated liquid alkali metal and hydrogen. The heated liquid alkali metal is recycled to the dehydrogenation zone to provide heat. The hydrocarbon stream containing dehydrogenated hydrocarbons is contacted in a selective adsorbent zone with an adsorbent to produce a stream containing dehydrogenated hydrocarbons and a stream containing unconverted dehydrogenatable hydrocarbons which is recycled to the dehydrogenation zone.

There is a steadily increasing demand for technology which is capable of producing olefins from dehydrogenatable hydrocarbons containing from 2 to about 18 carbons atoms. Dehydrogenating hydrocarbons is an important commercial hydrocarbon conversion process because of the great demand for dehydrogenated hydrocarbons for the manufacture of various chemical products such as detergents, high octane motor fuels, pharmaceutical products, plastics, synthetic rubbers, polymerization and other products well known to those skilled in the art. Processes for the dehydrogenation of light acyclic hydrocarbons are well known to those skilled in the hydrocarbon conversion arts.

INFORMATION DISCLOSURE

In U.S. Pat. No. 4,675,465 (Fanelli et al.), a process is disclosed for dehydrogenating reactants wherein a reactant comprising a hydrocarbon is exposed to a solid admixture of a platinum on alumina catalyst for dehydrogenation and a material to remove at least one hydrogen atom from the hydrocarbon and form a material hydride. The material is selected from the group of metals, alloys and intermetallic compounds having a negative free energy of formation for a hydrided product. The '465 patent fails to disclose the contacting of a dehydrogenatable hydrocarbon with a liquid comprising an alkali metal in a dehydrogenation zone to produce a dehydrogenated hydrocarbon and an alkali metal hydride.

Other prior art processes for the dehydrogenation of paraffins suffered under several disadvantages including poor olefin product yields and poor catalyst life caused by the relatively high catalyst inlet temperature required to supply the essential heat of reaction and the relatively high cost of the required multi-stage reactors and their attendant interheaters.

BRIEF SUMMARY OF THE INVENTION

The invention provides a process for the dehydrogenation of a dehydrogenatable hydrocarbon by contacting the dehydrogenatable hydrocarbon with a liquid comprising an alkali metal in a dehydrogenation zone to produce a hydrocarbon stream containing a dehydrogenated hydrocarbon and an alkali metal hydride. At least a portion of the resulting alkali metal hydride is heated to produce a heated liquid alkali metal and hydrogen. At least a portion of the heated liquid alkali metal is recycled to the dehydrogenation zone to provide heat. The hydrocarbon stream containing dehydrogenated hydrocarbons is contacted in a selective adsorbent zone with an adsorbent to produce a stream containing dehydrogenated hydrocarbons and a stream containing unconverted dehydrogenatable hydrocarbons which is recycled to the dehydrogenation zone. The present invention provides a convenient and economical process for the production of olefinic hydrocarbons. Important elements of the process are the facile removal of hydrogen from the dehydrogenation zone which minimizes chemical equilibrium constraints and simplifies the recovery of the resulting olefinic hydrocarbons and the supply of heat to the dehydrogenation zone without the need to heat the dehydrogenatable hydrocarbon reactants to reaction temperature prior to entering the reaction zone. In addition, unconverted dehydrogenatable hydrocarbons are recovered and recycled to the dehydrogenation zone.

One embodiment of the present invention may be characterized as a process for the dehydrogenation of a dehydrogenatable hydrocarbon which process comprises: (a) contacting the dehydrogenatable hydrocarbon with a liquid comprising an alkali metal in a dehydrogenation zone at dehydrogenation conditions to produce a stream comprising a dehydrogenated hydrocarbon and an unconverted dehydrogenatable hydrocarbon, and an alkali metal hydride; (b) removing and heating at least a portion of the alkali metal hydride from the dehydrogenation zone to produce a heated liquid alkali metal and hydrogen; (c) recycling at least a portion of the heated liquid alkali metal to the dehydrogenation zone in step (a); (d) contacting at least a portion of the stream comprising dehydrogenated hydrocarbon and unconverted dehydrogenatable hydrocarbon with a selective adsorbent in a selective adsorbent zone to selectively adsorb dehydrogenated hydrocarbon and produce a stream comprising an unconverted dehydrogenatable hydrocarbon and to desorb the selective adsorbent and produce a stream comprising an unconverted dehydrogenatable hydrocarbon; (e) recycling at least a portion of the stream comprising unconverted dehydrogenatable hydrocarbon recovered in step (d) to the dehydrogenation zone in step (a); and (f) recovering the stream comprising the dehydrogenated hydrocarbon.

BRIEF DESCRIPTION OF THE DRAWING

The drawing is a simplified process flow diagram of a preferred embodiment of the present invention.

DETAILED DESCRIPTION OF THE INVENTION

The present invention provides a process for the dehydrogenation of a dehydrogenatable hydrocarbon. The dehydrogenatable hydrocarbon is contacted with a liquid containing an alkali metal in a dehydrogenation zone at dehydrogenation conditions to produce a stream containing dehydrogenated hydrocarbon and unconverted dehydrogenatable hydrocarbon, and an alkali metal hydride. The stream containing dehydrogenated hydrocarbon and unconverted dehydrogenatable hydrocarbon is preferably removed from the dehydrogenation zone in gaseous phase and the alkali metal hydride is removed from the dehydrogenation zone in a liquid phase. The alkali metal hydride is subsequently heated to remove hydrogen, thereby providing heated metal which may be recycled to serve as a hydrogen sponge and to provide heat for the endothermic dehydrogenation reaction in the dehydrogenation zone. The stream containing dehydrogenated hydrocarbon and unconverted dehydrogenatable hydrocarbon is removed from the dehydrogenation zone and contacted with a selective adsorbent in a selective adsorbent zone to produce a stream containing dehydrogenated hydrocarbon and a stream containing an unconverted dehydrogenatable hydrocarbon.

Paraffin dehydrogenation is an endothermic reaction and the heat of reaction for the formation of a mono-olefin is approximately 30 kilocalories/gram mol for a feed that may vary from $C_2$ (ethane) to $C_{18}$ paraffins. Therefore, when olefins are produced from paraffins, the heat of reaction must be supplied from an external source.

In accordance with the present invention, the dehydrogenatable hydrocarbon charge stock may contain from 2 carbons to about 18 carbon atoms. Representative members of this class are ethane, propane, butane, pentane, hexane, heptane and mixtures thereof. A particularly important class of charge stocks include propane, butane, pentane and mixtures thereof and which are readily prepared by the fractionation of relatively low boiling point hydrocarbon fractions.

The dehydrogenatable hydrocarbon feedstock is introduced into a dehydrogenation zone and contacted with a liquid comprising an alkali metal at dehydrogenation conditions to produce a dehydrogenated hydrocarbon and an alkali metal hydride. In a preferred embodiment, the contacting is performed by bubbling a gaseous dehydrogenatable hydrocarbon through a liquid phase comprising an alkali metal. In another preferred embodiment, the contacting is performed by intimately admixing a liquid dehydrogenatable hydrocarbon with a liquid phase comprising an alkali metal. Preferred alkali metals are lithium and sodium. When the reacted hydrocarbons are in the gaseous phase, the gaseous phase is removed from a vapor-liquid separation zone and when the reacted hydrocarbons are in the liquid phase, the liquid hydrocarbon phase is separated from the alkali metal liquid phase in a liquid—liquid separator. Preferred dehydrogenation conditions include a pressure from atmospheric to about 500 psig (3447 kPa gauge), a temperature from about 392° F. (200° C.) to about 1310° F. (700° C.), and a hydrocarbon to alkali metal mol ratio from about 1 to about 20.

A resulting hydrocarbon stream containing dehydrogenated hydrocarbons and unconverted dehydrogenatable hydrocarbon is removed from the dehydrogenation zone and recovered. In accordance with the present invention, the resulting hydrocarbon stream is separated to recover the olefin hydrocarbons and to produce a stream of unreacted hydrocarbons which may then be recycled to the dehydrogenation zone to produce additional olefin hydrocarbons.

A liquid stream containing alkali metal hydride is removed from the dehydrogenation zone and is heated to produce a heated liquid alkali metal stream and hydrogen. In order to regenerate the alkali metal hydride stream, it is preferably heated in a heating zone to a temperature in the range from about 752° F. (400° C.) to about 1562° F. (850° C.). The circulation rate of the heated liquid alkali metal stream is preferably selected to ensure that the required heat is subsequently supplied to the dehydrogenation zone to maintain the desired dehydrogenation reaction temperature.

In accordance with the present invention, the alkali metal may be selected from the group consisting of lithium, sodium, potassium, rubidium, cesium, and admixtures thereof. In one embodiment of the present invention, the circulating liquid stream containing alkali metal and/or alkali metal hydride may be transferred to and from the dehydrogenation zone and the heating zone by means of pumps, gravity or thermal siphon.

A resulting hydrocarbon stream containing dehydrogenated hydrocarbons and unconverted dehydrogenatable hydrocarbon is removed from the dehydrogenation zone and contacted with a selective adsorbent in a selective adsorbent zone to produce a stream containing a dehydrogenated hydrocarbon and a stream containing an unconverted dehydrogenatable hydrocarbon.

Adsorptive separation requires the sequential performance of three basic steps. The adsorbent must first be brought into contact with a feed stream at adsorption-promoting conditions. This adsorption step should continue for a time sufficient to allow the adsorbent to collect a near equilibrium amount of the preferentially adsorbed dehydrogenated hydrocarbon. The second basic step is the contacting of the adsorbent bearing both dehydrogenated hydrocarbon and dehydrogenatable hydrocarbon with a material which displaces the latter from the adsorbent. The second step is performed in a manner which results in the adsorbent containing significant quantities of only the dehydrogenated hydrocarbon and the material used to displace the dehydrogenatable compounds.

The third basic step is the desorption of the dehydrogenated hydrocarbon from the adsorbent. This may be performed by changing the conditions of temperature and pressure, but preferably it is performed by contacting the adsorbent with a desorbent stream. The desorbent stream contains a chemical compound capable of displacing or desorbing the dehydrogenated hydrocarbon from the adsorbent to thereby release the dehydrogenated hydrocarbon and prepare the adsorbent for another adsorption step.

The contacting of the adsorbent with either the adsorbent feed stream or the desorbent stream leaves the interstitial void spaces between the adsorbent particles filled with the components of these particular streams. When the next contacting step begins, this residual liquid is admixed into the entering liquid. This results in the effluent streams removed from the adsorbent bed being mixtures of compounds from the two or more streams which are passed into the adsorbent bed. In the present invention, two such effluent streams are produced. They comprise a mixture of the desorbent and the dehydrogenated hydrocarbon and a mixture of the desorbent with dehydrogenatable hydrocarbons. In order to obtain a high purity product stream of the dehydrogenatable hydrocarbon which is suitable for recycle to the dehydrogenation zone, it is necessary to fractionate the stream to recover the desorbent and produce the recycle stream. In order to obtain a high purity product stream of the dehydrogenated hydrocarbon and to recover the desorbent, it is also necessary to fractionate the mixture. The two effluent streams are therefore fractionated in two separate fractionation columns referred to as the raffinate column and the extract column.

The sequential adsorption and desorption steps of an adsorptive separating procedure may be performed using a fixed bed of adsorbent having fixed inlet and outlet points at opposite ends of the adsorbent bed. However, it is preferred to use a simulated moving bed of adsorbent. These benefits include the continuous production of a high purity recycle stream and product stream. Preferably, the countercurrent flow of the bed of solid adsorbent and the various entering liquid streams, such as the feed and desorbent streams, is simulated.

Two separate actions are involved in this simulation. The first of these is the maintenance of a net fluid flow through the bed of adsorbent in a direction opposite to the direction of simulated movement of the adsorbent. This is performed through the use of a pump operatively connected in a manner to achieve this circulation along the length of the entire bed of adsorbent. The second action involved in simulating the movement of the adsorbent is the periodic actual movement of the location of the various zones, such as the adsorption zone, along the length of the bed of adsorbent. This actual movement of the location of the various zones is performed gradually in a unidirectional pattern by periodically advancing the points at which the entering streams enter the adsorbent bed and the points at which the effluent streams are withdrawn from the adsorbent bed. It is only the locations of the zones as defined by the respective feed and withdrawal points along the bed of adsorbent which are changed. The adsorbent bed itself is fixed and does not move.

The bed of adsorbent may be contained in one or more separate interconnected vessels. At a large number of points along the length of the bed of adsorbent, the appropriate openings and conduits are provided to allow the addition or withdrawal of liquid. At each of these points, there is preferably provided a constriction of the cross-section of the bed of adsorbent by a liquid distributor-collector. These distributor-collectors serve to aid in the establishment and maintenance of plug flow of the fluids along the length of the bed of adsorbent. The two points at which any one stream enters and the corresponding effluent stream leaves the bed of adsorbent are separated from each other by at least two or more potential fluid feed or withdrawal points which are not being used. For instance, the feed stream may enter the adsorption zone at one point and flow past nine potential withdrawal points and through nine distributor-collectors before reaching the point at which it is withdrawn from the adsorbent bed as the raffinate stream.

The gradual and incremental movement of the adsorption zone is achieved by periodically advancing the actual points of liquid addition or withdrawal to the next available potential point. That is, in each advance of the adsorption zone, the boundaries marking the beginning and the end of each zone will move by the relatively uniform distance between two adjacent potential points of liquid addition or withdrawal. The majority of the zone is unaffected and remains intact since the zone extends past several of these fluid transfer points.

The switching of the fluid flows at these many different locations may be achieved by a multiple-valve manifold or by the use of a multiple-port rotary valve. A central digital controller is preferably used to regulate the operation of the rotary valve or manifold. Further details on the operation of a simulated moving bed of adsorbent and the preferred rotary valves may be obtained from U.S. Pat. Nos. 2,985,589; 3,201,491; 3,291,726; 3,732,325; 3,040,777; 3,422,848; 3,192,954; 2,957,485; 3,131,232; 3,268,604 and 3,268,605.

The present process may be practiced by using any suitable type of commercially operable and practical selective adsorbent. A preferred adsorbent comprises a selective zeolite commonly referred to as a molecular sieve. The preferred zeolites comprise synthetic crystalline aluminosilicates. Since the pure zeolites are relatively soft and powdery, the commercially used molecular sieves comprise a binder such as clay or alumina to produce a stronger and more attrition-resistant adsorbent particle. The adsorbent particles preferably have a size range of about 20 to about 40 mesh.

The particular adsorbent selected and utilized in the present invention will depend on the particular hydrocarbonaceous materials which it is desired to separate. The selective adsorption of olefinic hydrocarbons from saturated hydrocarbons may be performed using a copper-exchanged Type Y zeolite as described in U.S. Pat. No. 3,720,604.

Although adsorptive separation can be operated with both vapor-phase and liquid-phase conditions, the use of liquid-phase conditions is preferred. Adsorption-promoting conditions therefore include a pressure sufficient to maintain all of the compounds present in the adsorbent bed as liquids. A pressure from atmospheric to about 50 atmospheres may be employed with the pressure preferably being between 1 and about 32 atmospheres gauge. Suitable operating temperatures range from 40° C. to about 250° C.

In accordance with the present invention, any suitable desorbent may be selected and utilized which is capable of desorbing the dehydrogenated hydrocarbon (extract component) from the bed of the adsorbent. It is preferred that the desorbent has a boiling point or boiling range such that the dehydrogenated hydrocarbon may be separated and recovered from the desorbent via fractionation. Preferred desorbents may be selected from the group consisting of hexene, octene and decene.

DETAILED DESCRIPTION OF THE DRAWING

With reference now to the drawing, a dehydrogenatable hydrocarbon feed stream is introduced via conduit 1 and is admixed with a recycle dehydrogenatable hydrocarbon stream supplied via conduit 13 and the resulting admixture is introduced into dehydrogenation zone 3 via conduit 2 and contacted with a heated liquid stream containing alkali metal which is introduced via conduit 8 into dehydrogenation zone 3. A resulting gaseous hydrocarbon stream containing olefin hydrocarbons is removed from dehydrogenation zone 3 via conduit 10 and introduced into adsorption zone 11. A resulting dehydrogenated hydrocarbon stream is removed from adsorption zone 11 via conduit 12 and recovered. A dehydrogenatable hydrocarbon stream is recovered from adsorption zone 11 via conduit 13 and recycled as described hereinabove. A liquid stream containing alkali metal hydride is removed from dehydrogenation zone 3 via conduit 4 and introduced into heat exchanger 5. A heated effluent from heat exchanger 5 is transported via conduit 6 and introduced into vapor-liquid separator 7. A gaseous stream containing molecular hydrogen is removed from vapor-liquid separator 7 via conduit 9. A liquid stream containing alkali metal is removed from vapor-liquid separator 7 via conduit 8 and introduced into dehydrogenation zone 3 as described hereinabove.

The process of the present invention is further demonstrated by the following illustrative embodiment. This illustrative embodiment is, however, not presented to unduly limit the process of this invention, but to further illustrate the advantages of the hereinabove-described embodiment. The following data were not obtained by the actual performance of the present invention, but are considered prospective and reasonably illustrative of the expected performance of the invention.

ILLUSTRATIVE EMBODIMENT

A fresh feed stream of pure isobutane in an amount of 100 mass units per hour is combined with an unconverted isobutane recycle stream in an amount of 2000 mass units per hour and the resulting admixture is bubbled through a liquid containing lithium at a temperature of 932° F. (500°

C.) and a pressure of 50 psig (345 kPa gauge) in a dehydrogenation zone. A gaseous effluent having the characteristics presented in Table 1 is continuously withdrawn from the dehydrogenation zone and introduced into an adsorptive separation zone containing a copper-exchanged Type Y zeolite. A stream of isobutane in an amount of 2000 mass units per hour is recovered from the adsorptive separation zone and recycled as described hereinabove. An isobutylene stream in an amount of 100 mass units per hour is recovered from the adsorptive separation zone. A liquid stream containing lithium hydride is removed from the dehydrogenation zone and heated to produce hydrogen and a liquid stream containing lithium which is recycled to the dehydrogenation zone to provide the heat of reaction and hydrogen sponge function.

TABLE 1

| DEHYDROGENATION ZONE EFFLUENT ANALYSIS | |
| --- | --- |
| Isobutane, weight percent | 94.5 |
| Propane, weight percent | 0.5 |
| Isobutylene, weight percent | 4.5 |
| Hydrogen, weight percent | 0 |

The foregoing description, drawing and illustrative embodiment clearly illustrate the advantages encompassed by the method of the present invention and the benefits to be afforded with the use thereof.

What is claimed:

1. A process for the dehydrogenation of a dehydrogenatable hydrocarbon which process comprises:
   (a) contacting said dehydrogenatable hydrocarbon with a liquid comprising an alkali metal in a dehydrogenation zone at dehydrogenation conditions to produce a stream comprising a dehydrogenated hydrocarbon and an unconverted dehydrogenatable hydrocarbon, and an alkali metal hydride;
   (b) removing and heating at least a portion of said alkali metal hydride from said dehydrogenation zone to produce a heated liquid alkali metal and hydrogen;
   (c) recycling at least a portion of said heated liquid alkali metal to said dehydrogenation zone in step (a);
   (d) contacting at least a portion of said stream comprising dehydrogenated hydrocarbon and unconverted dehydrogenatable hydrocarbon with a selective adsorbent in a selective adsorbent zone to selectively adsorb dehydrogenated hydrocarbon and produce a stream comprising an unconverted dehydrogenatable hydrocarbon and to desorb said selective adsorbent and produce a stream comprising an unconverted dehydrogenatable hydrocarbon;
   (e) recycling at least a portion of said stream comprising unconverted dehydrogenatable hydrocarbon recovered in step (d) to said dehydrogenation zone in step (a); and
   (f) recovering said stream comprising dehydrogenated hydrocarbon.

2. The process of claim 1 wherein said alkali metal is selected from the group consisting of lithium, sodium, potassium, rubidium and cesium.

3. The process of claim 1 wherein said dehydrogenation conditions include a pressure from about atmospheric to about 500 psig (3447 kPa gauge), a temperature from about 392° F. (200° C.) to about 1310° F. (700° C.), a hydrocarbon to alkali metal mol ratio from about 1 to about 20.

4. The process of claim 1 wherein said alkali metal hydride is heated to a temperature in the range from about 752° F. (400° C.) to about 1562° F. (850° C.) to produce said heated liquid alkali metal and said hydrogen.

5. The process of claim 1 wherein said dehydrogenatable hydrocarbon is an alkane having from 2 to about 18 carbon atoms.

6. The process of claim 1 wherein said dehydrogenated hydrocarbon is an alkene.

7. The process of claim 1 wherein said dehydrogenated hydrocarbon in an alkyne.

8. The process of claim 1 wherein said selective adsorbent zone utilizes a simulated moving bed of adsorbent.

9. The process of claim 1 wherein said selective adsorbent comprises crystalline aluminosilicate.

10. The process of claim 1 wherein said selective adsorbent comprises a copper-exchanged Type Y zeolite.

11. The process of claim 1 wherein said selective adsorbent zone is conducted at adsorption conditions including a pressure from atmospheric to about 50 atmospheres and a temperature from about 104° F. (40° C.) to about 482° F. (250° C.).

* * * * *